United States Patent [19]

Okabe

[11] Patent Number: 4,755,029

[45] Date of Patent: Jul. 5, 1988

[54] OBJECTIVE FOR AN ENDOSCOPE

[75] Inventor: Minoru Okabe, Tokyo, Japan

[73] Assignee: Olympus Optical Co., Ltd., Tokyo, Japan

[21] Appl. No.: 51,538

[22] Filed: May 19, 1987

[30] Foreign Application Priority Data

May 22, 1986 [JP] Japan .................................. 61-116230

[51] Int. Cl.$^4$ .................................................. G02B 6/18
[52] U.S. Cl. .................................. 350/413; 350/96.31
[58] Field of Search .................. 350/413, 96.29, 96.30, 350/96.31

[56] References Cited

U.S. PATENT DOCUMENTS

| | | | |
|---|---|---|---|
| 3,801,181 | 4/1974 | Kitano et al. | 350/413 |
| 4,101,196 | 7/1978 | Imai | 350/413 X |
| 4,515,444 | 5/1985 | Prescott et al. | 350/413 |
| 4,641,927 | 2/1987 | Prescott et al. | 350/413 |

FOREIGN PATENT DOCUMENTS

| | | |
|---|---|---|
| 47-28061 | 7/1972 | Japan . |
| 49-121547 | 11/1974 | Japan . |
| 60-140309 | 7/1985 | Japan . |
| 60-225816 | 11/1985 | Japan . |

*Primary Examiner*—John K. Corbin
*Assistant Examiner*—Scott J. Sugarman
*Attorney, Agent, or Firm*—Cushman, Darby & Cushman

[57] ABSTRACT

An objective for an endoscope comprising a GRIN lens whose surface on the object side is arranged as a planar surface or convex surface and whose surface on the image side is arranged as a convex surface, the objective for an endoscope having an extremely small outer diameter and a wide field angle.

20 Claims, 13 Drawing Sheets

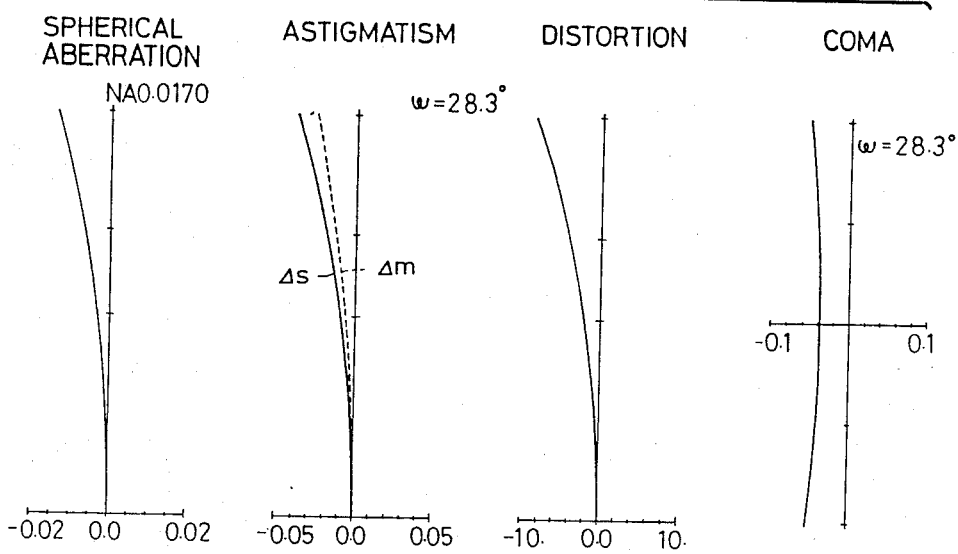
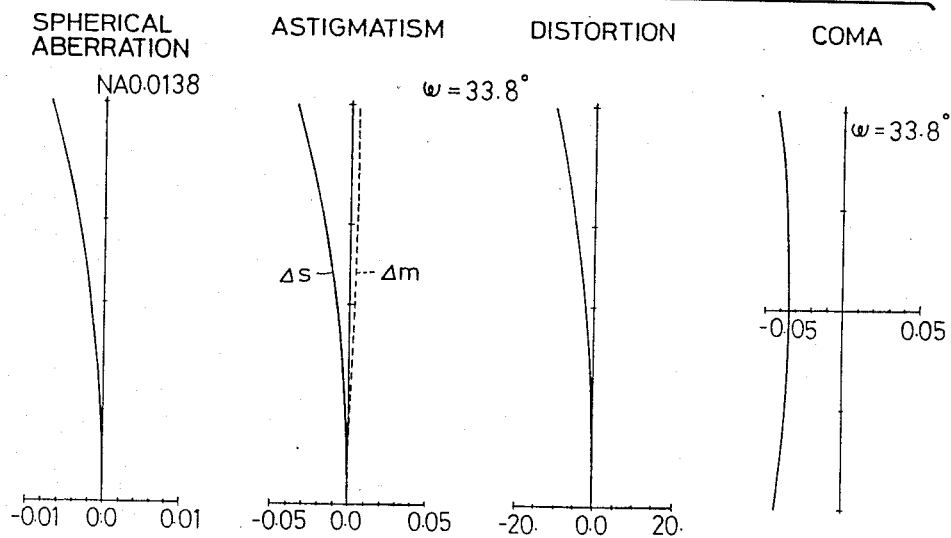

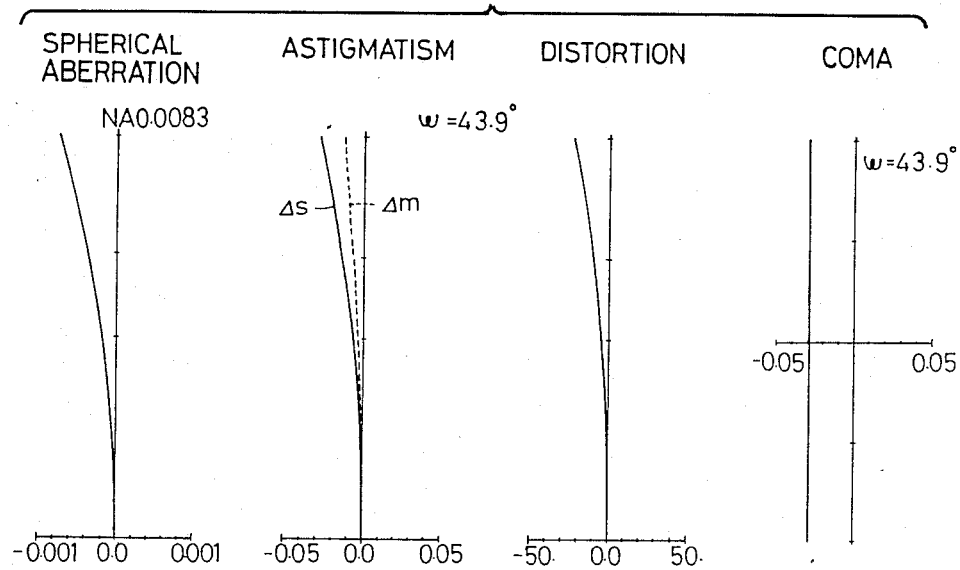
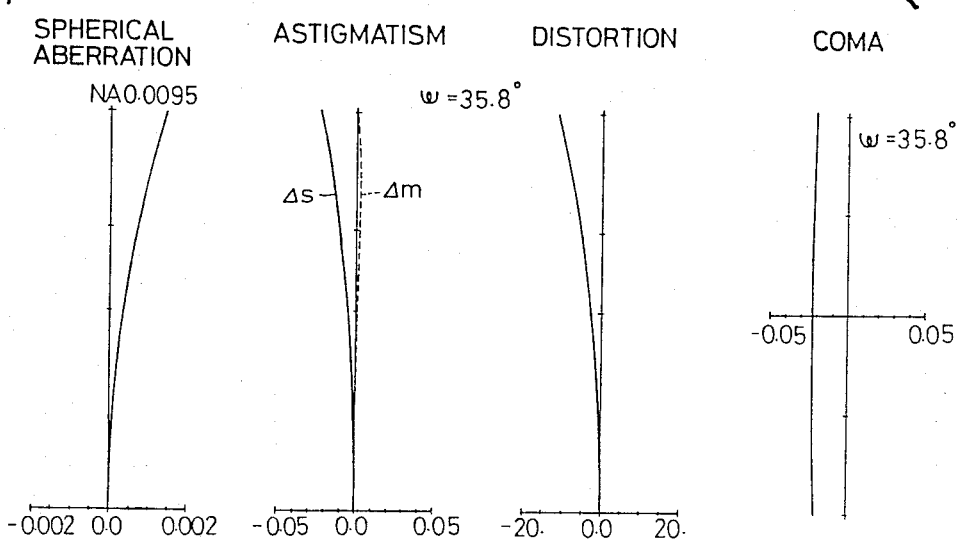

OBJECTIVE FOR AN ENDOSCOPE

BACKGROUND OF THE INVENTION (a) Field of the Invention

The present invention relates to an objective for an endoscope and, more particularly, to an objective for an endoscope wherein an inhomogeneous medium is used.

(b) Description of the Prior Art

A retrofocus type objective as shown in FIG. 1 and disclosed by Japanese published unexamined patent application No. 121547/74 is known as an objective for an endoscope.

In recent years, it is required to make the endoscopes smaller and smaller in the diameter. This means that an objective with an extremely small outer diameter is required necessarily.

For an objective with an extremely small outer diameter, it is very difficult to use a plural number of lenses as in case of said known retrofocus type objective due to the reasons related to assembly. Therefore, it is known to arrange that an objective comprises one positive lens as shown in FIG. 2. However, an objective comprising one positive lens has a disadvantage that aberrations are caused largely and, consequently, the field angle is somewhat limited and cannot be made wide.

To obtain an objective with a small outer diameter which supersedes said known objective comprising one positive lens, it may be considered to use a lens made of an inhomogeneous medium as disclosed by Japanese published examined patent application No. 28061/72 and as shown in FIG. 3. For example, it may be considered to use a graded refractive index lens (hereinafter referred to as a GRIN lens) whose refractive index is expressed by the formula shown below when the refractive index of the central portion of said GRIN lens is represented by reference symbol $n_0$ and the radial distance from the optical axis is represented by reference symbol r:

$$n^2(r) = n_0^2\{1 - (gr)^2 + h_4(gr)^4 + h_6(gr)^6 + \ldots\}$$

where, reference symbol g represents a parameter showing the degree of the gradient of the refractive index, and reference symbols $h_4$, $h_6$ ... respectively represent the coefficients of distribution of refractive indices in the terms of the fourth order, sixth order and so on.

However, said GRIN lens has a disadvantage that the field angle is decided by the distribution of refractive indices thereof, and it is impossible to make the field angle wide.

SUMMARY OF THE INVENTION

It is, therefore, a primary object of the present invention to provide an objective for an endoscope having a simple composition, an extremely small outer diameter and a wide field angle.

The basic composition of the objective for an endoscope according to the present invention is shown in FIG. 4.

To attain the above-mentioned primary object, the objective for an endoscope according to the present invention is composed as described below.

That is, the objective for an endoscope according to the present invention is arranged to comprise a GRIN lens with an extremely small outer diameter and an aperture stop located on the object side of said GRIN lens, said GRIN lens being arranged that the surface on the object side is formed as a planar surface or convex surface and the surface on the image side is formed as a convex surface and that the refractive index n of said GRIN lens is expressed by the formula shown below when the refractive index of the central portion of said GRIN lens is represented by reference symbol $n_0$ and the radial distance from the optical axis is represented by reference symbol r:

$$n^2(r) = n_0^2\{1 - (gr)^2 + h_4(gr)^4 + h_6(gr)^6 + \ldots\}$$

where, reference symbol g represents a parameter showing the degree of the gradient of the refractive index, and reference symbols $h_4$, $h_6$, ... respectively represent the coefficients of distribution of refractive indices in the terms of the fourth order, sixth order and so on, said objective for an endoscope according to the present invention being arranged to fulfill the conditions (1), (2) and (3) shown below:

$$1.4 \geq |2I/\phi| \geq 0.6 \quad (1)$$

$$0.5 \leq \frac{1 - n_0}{R_2 \cdot n_0 \cdot g \cdot \sin(gZ)} \leq 3 \quad (2)$$

$$|R_2/R_1| \leq 1.0 \quad (3)$$

where, reference symbol I represents the image height, reference symbol $\phi$ represents the outer diameter of the GRIN lens, reference symbol Z represents the thickness of the central portion of the GRIN lens, reference symbol $R_1$ represents the radius of curvature of the surface on the object side of the GRIN lens, and reference symbol $R_2$ represents the radius of curvature of the surface on the image side of the GRIN lens.

By arranging at least one surface of the GRIN lens as a convex surface, the objective for an endoscope according to the present invention is arranged to eliminate the disadvantage of the known objective for an endoscope comprising one positive lens as shown in FIG. 2 and of the known objective for an endoscope comprising a GRIN lens as shown in FIG. 3, i.e., the disadvantage that the field angle cannot be made wide.

In other words, the objective for an endoscope according to the present invention is arranged that at least one surface of the GRIN lens, whose medium itself has power, is formed as a convex surface in the range that offaxial aberrations to be caused by said GRIN lens, i.e., coma and curvature of field, are not undercorrected, said objective for an endoscope being thereby arranged that the power of the lens (the GRIN lens) as a whole is made strong so that the field angle is thereby made wide.

As the outer diameter of the endoscope should be made small, the objective constituting the endoscope should be arranged to comprise a single lens whose outer diameter is extremely small. To make the field angle wide and to make the outer diameter of the endoscope small at the same time, it is necessary to arrange that the image height I and outer diameter $\phi$ of the single lens fulfill the condition (1) shown before. If the value of $|2I/\phi|$ becomes smaller than the lower limit of the condition (1), it is difficult to make the field angle wide. If the value of $|2I/\phi|$ becomes larger than the upper limit of the condition (1), it is difficult to make the outer diameter of the endoscope small.

In case of the objective according to the present invention, the image height, i.e., the field angle, is extremely large compared with objectives for pick-up devices for optical disks and the like. Therefore, the objective according to the present invention is arranged to fulfill the conditions (2) and (3) in order to make the field angle wide in the range that offaxial aberrations are not undercorrected.

The condition (2) defines the value obtained when the power $(1-n_0)/R_2$ of the surface on the image side of the single lens is divided by the power $n_0 \cdot g \cdot \sin(gZ)$ of the medium itself which has the power due to the fact that the medium itself has the distribution of refractive indices therein. In other words, the condition (2) defines the ratio between the former power and the latter power.

If said ratio becomes smaller than the lower limit of the condition (2), the power of the surface on the image side of the single lens becomes too weak, and it is difficult to make the field angle wider than the value decided by the distribution of refractive indices. If said ratio becomes larger than the upper limit of the condition (2), the power of the surface on the image side of the single lens becomes too strong, and aberrations will be undercorrected.

The condition (3) defines the value obtained when the radius of curvature $R_2$ of the surface on the image side of the single lens is divided by the radius of curvature $R_1$ of the surface on the object side of said single lens. If the value of $|R_2/R_1|$ becomes larger than 1.0 defined by the condition (3), i.e., if $R_1$ becomes smaller than $R_2$, the power of the surface on the object side becomes too strong, and offaxial aberrations will be undercorrected.

In addition to the conditions described so far, it is preferable to arrange that the objective for an endoscope according to the present invention further fulfills the conditions (4), (5) and (6) shown below because it is then possible to obtain a more favourable objective for an endoscope which serves to attain the object of the present invention.

$$|R_2/I| \leq 3 \quad (4)$$

$$g \geq 0.58 \quad (5)$$

$$h_4 \geq 0 \quad (6)$$

Out of respective conditions shown in the above, the conditions (4) and (5) respectively serve to make the power of the single lens, whose outer diameter is extremely small, strong and to thereby make the field angle wide.

When, either the condition (4) or the condition (5) is not fulfilled, it is difficult to make the field angle wide.

The condition (6) relates to the coefficient $h_4$ of distribution of refractive indices in the term of the fourth order. When it is arranged that the value of $h_4$ becomes positive as defined by the condition (6), the gradient of distribution of refractive indices in the marginal portion of the medium becomes comparatively gentle, and the power of the marginal portion of the medium becomes weak. Therefore, it is possible to correct offaxial aberrations to be caused by the convex surface of the single lens. On the contrary, when the value of $h_4$ becomes negative, offaxial aberrations will be undercorrected.

As shown in FIGS. 4 and 5, an image fiber bundle 2 may be generally considered as a means for optically transmitting the image formed by the single lens 1 constituting the objective according to the present invention. In that case, it is preferable to arrange that the principal ray 3 enters the light entrance surface of the image fiber bundle 2 substantially vertically. For this purpose, the aperture stop S should be provided on the object side of the single lens.

The case is the same as above also when a rod-like GRIN lens 4 as shown in FIG. 6 or a lens system 5 as shown in FIG. 7 is provided, instead of the image fiber bundle 2, as the means for optically transmitting the image.

On the other hand, in case of an electronic endoscope wherein a solid-state image sensor 6 is used as the means for transmitting the image as shown in FIG. 8, the image will be properly transmitted even when the principal ray 3' is obliquely incident on the solid-state image sensor 6.

BRIEF DESCRIPTION OF THE DRAWINGS

FIGS. 16 through 33 respectively show graphs illustrating aberration curves of Embodiments 1 through 18 of the present invention.

DETAILED DESCRIPTION OF THE PREFERRED EMBODIMENTS

Figure 1:
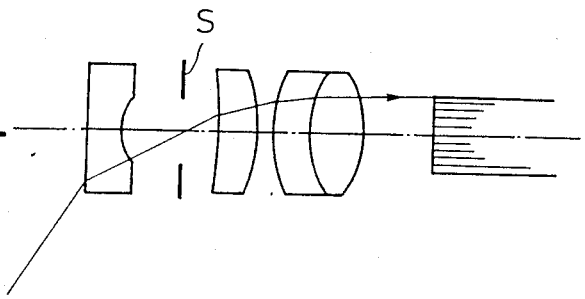
FIGS. 1, 2 and 3 respectively show sectional views illustrating compositions of known objectives for endoscopes.
Figure 2:
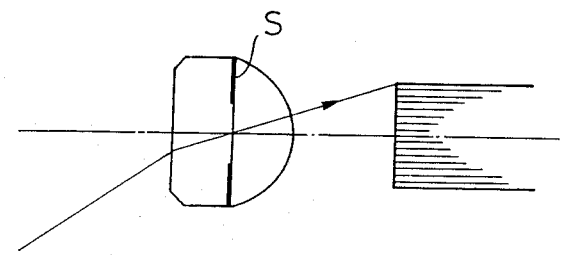
Figure 3:
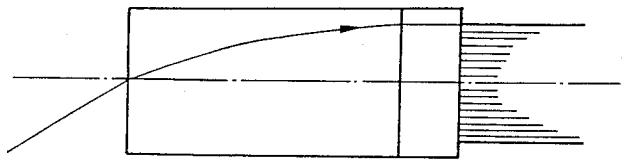
Figure 4:
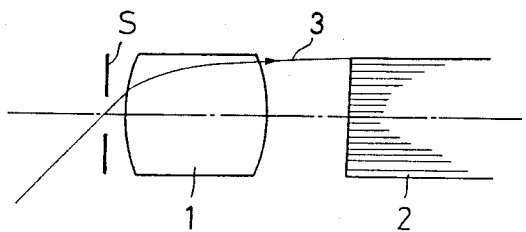
FIG. 4 shows a sectional view illustrating the basic composition of the objective for an endoscope according to the present invention.
Figure 5:
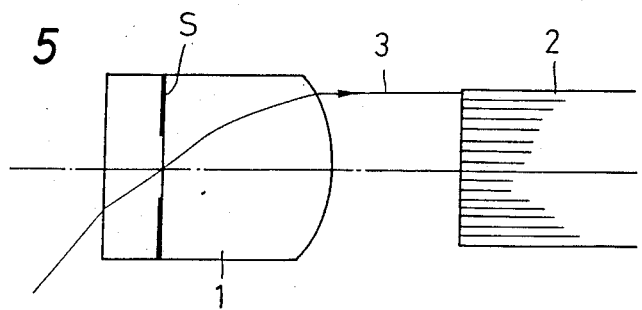
FIG. 5 shows a sectional view illustrating the composition of an example wherein the objective according to the present invention is applied to an endoscope in which an image fiber bundle is used.
Figure 6:
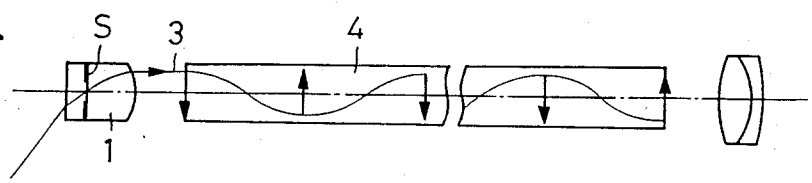
FIG. 6 shows a sectional view illustrating the composition of an example wherein the objective according to the present invention is applied to an endoscope in which a rod-like GRIN lens is used as an image transmission system.
Figure 7:
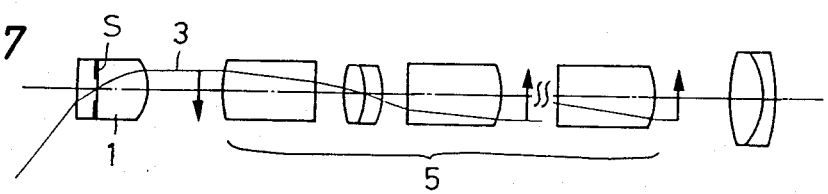
FIG. 7 shows a sectional view illustrating the composition of an example wherein the objective according to the present invention is applied to an endoscope which employs an image transmission optical system comprising homogeneous lenses.
Figure 8:
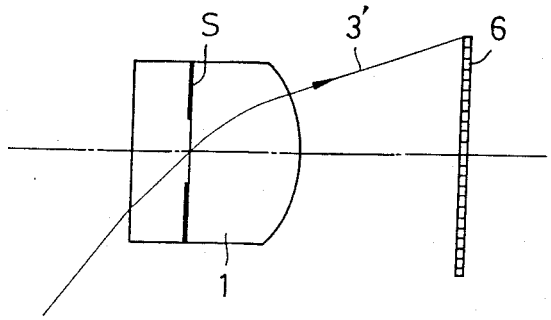
FIG. 8 shows a sectional view illustrating the composition of an example wherein the objective according to the present invention is applied to an electronic endoscope which employs a solid-state image sensor.

Now, the preferred embodiments of the objective for an endoscope according to the present invention are shown below.

Embodiment 1

| | | |
|---|---|---|
| f = 0.491, | F = 2.99, | $2\omega = 69.2°$ |
| I = 0.3, | $\phi = 0.6$ | |

$r_1 = \infty$ (stop)
$d_1 = 0$
$r_2 = \infty$ (= $R_1$)
$d_2 = 0.6632$   $n_1 = 1.6000$ (*)
$r_3 = -0.4500$ (= $R_2$)
$d_3 = 0.1900$
$r_4 = \infty$
$d_4 = 0.3000$   $n_2 = 1.51633$   $\nu_2 = 64.15$
$r_5 = \infty$ (Coefficients of power distribution of GRIN lens)
g = 1.0,   $h_4 = 0$,   $h_6 = 0$ $\left|\dfrac{2I}{\phi}\right| = 1.0$,   $\dfrac{1 - n_0}{R_2 \cdot n_0 \cdot g \cdot \sin(gZ)} = 1.354$ $\left|\dfrac{R_2}{I}\right| = 1.5$,   $\left|\dfrac{R_2}{R_1}\right| = 0$

Embodiment 2

| | | |
|---|---|---|
| f = 0.551, | F = 2.99, | $2\omega = 60.8°$ |
| I = 0.3, | $\phi = 0.6$ | |

$r_1 = \infty$ (stop)
$d_1 = 0$
$r_2 = \infty$ (= $R_1$)
$d_2 = 0.7363$   $n_1 = 1.6000$ (*)
$r_3 = -0.6000$ (= $R_2$)

(Coefficients of power distribution of GRIN lens)
g = 1.0,   $h_4 = 0$,   $h_6 = 0$ $\left|\dfrac{2I}{\phi}\right| = 1.0$,   $\dfrac{1 - n_0}{R_2 \cdot n_0 \cdot g \cdot \sin(gZ)} = 0.892$ $\left|\dfrac{R_2}{I}\right| = 2.0$,   $\left|\dfrac{R_2}{R_1}\right| = 0$

Embodiment 3

| | | |
|---|---|---|
| f = 0.589, | F = 2.99, | $2\omega = 56.6°$ |
| I = 0.3 | $\phi = 0.6$ | |

$r_1 = \infty$ (stop)
$d_1 = 0$
$r_2 = \infty$ (= $R_1$)
$d_2 = 0.7868$   $n_1 = 1.6000$ (*)
$r_3 = -0.7500$ (= $R_2$)

(Coefficients of power distribution of GRIN lens)
g = 1.0,   $h_4 = 0$,   $h_6 = 0$ $\left|\dfrac{2I}{\phi}\right| = 1.0$,   $\dfrac{1 - n_0}{R_2 \cdot n_0 \cdot g \cdot \sin(gZ)} = 0.706$ $\left|\dfrac{R_2}{I}\right| = 2.5$,   $\left|\dfrac{R_2}{R_1}\right| = 0$

Embodiment 4

| | | |
|---|---|---|
| f = 0.490, | F = 3.01, | $2\omega = 67.6°$ |
| I = 0.3, | $\phi = 0.65$ | |

$r_1 = \infty$ (stop)
$d_1 = 0$
$r_2 = \infty$ (= $R_1$)
$d_2 = 0.6774$   $n_1 = 1.6000$ (*)
$r_3 = -0.4500$ (= $R_2$)

(Coefficients of power distribution of GRIN lens)
g = 1.0,   $h_4 = 0$,   $h_6 = 0$ $\left|\dfrac{2I}{\phi}\right| = 0.923$,   $\dfrac{1 - n_0}{R_2 \cdot n_0 \cdot g \cdot \sin(gZ)} = 1.330$ $\left|\dfrac{R_2}{I}\right| = 1.5$,   $\left|\dfrac{R_2}{R_1}\right| = 0$

Embodiment 5

| | | |
|---|---|---|
| f = 0.310, | F = 2.99, | $2\omega = 111.9°$ |
| I = 0.3, | $\phi = 0.65$ | |

$r_1 = \infty$ (stop)
$d_1 = 0$
$r_2 = \infty$ (= $R_1$)
$d_2 = 0.6238$   $n_1 = 1.8000$ (*)
$r_3 = -0.4500$ (= $R_2$)

(Coefficients of power distribution of GRIN lens)
g = 1.5,   $h_4 = 2.5$,   $h_6 = -0.5$ $\left|\dfrac{2I}{\phi}\right| = 0.923$,   $\dfrac{1 - n_0}{R_2 \cdot n_0 \cdot g \cdot \sin(gZ)} = 1.818$ $\left|\dfrac{R_2}{I}\right| = 1.5$,   $\left|\dfrac{R_2}{R_1}\right| = 0$

Embodiment 6

| | | |
|---|---|---|
| f = 0.203, | F = 2.98, | $2\omega = 83.9°$ |
| I = 0.15, | $\phi = 0.35$ | |

$r_1 = \infty$
$d_1 = 0$   $n_1 = 1.51633$   $\nu_1 = 64.15$
$r_2 = \infty$ (stop)
$d_2 = 0$
$r_3 = \infty$ (= $R_1$)
$d_3 = 0.3930$   $n_2 = 1.65000$ (*)
$r_4 = -0.2400$ (= $R_2$)

(Coefficients of power distribution of GRIN lens)
g = 2.5,   $h_4 = 1.5$,   $h_6 = 1$ $\left|\dfrac{2I}{\phi}\right| = 0.857$,   $\dfrac{1 - n_0}{R_2 \cdot n_0 \cdot g \cdot \sin(gZ)} = 0.789$ $\left|\dfrac{R_2}{I}\right| = 1.6$,   $\left|\dfrac{R_2}{R_1}\right| = 0$

Embodiment 7

| | | |
|---|---|---|
| f = 0.219, | F = 2.99, | $2\omega = 77.8°$ |
| I = 0.15, | $\phi = 0.35$ | |

$r_1 = \infty$ (stop)
$d_1 = 0$
$r_2 = \infty$ (= $R_1$)
$d_2 = 0.3192$   $n_1 = 1.65000$ (*)
$r_3 = -0.2000$ (= $R_2$)

(Coefficients of power distribution of GRIN lens)
g = 2,   $h_4 = 4$,   $h_6 = -1.5$ $\left|\dfrac{2I}{\phi}\right| = 0.857$,   $\dfrac{1 - n_0}{R_2 \cdot n_0 \cdot g \cdot \sin(gZ)} = 1.573$ $\left|\dfrac{R_2}{I}\right| = 1.333$   $\left|\dfrac{R_2}{R_1}\right| = 0$

Embodiment 8

| | | |
|---|---|---|
| f = 0.734, | F = 3.00, | $2\omega = 61.4°$ |
| I = 0.4, | $\phi = 1.0$ | |

$r_1 = \infty$
$d_1 = 0.4000$   $n_1 = 1.51633$   $\nu_1 = 64.15$
$r_2 = \infty$ (stop)
$d_2 = 0$
$r_3 = \infty$ (= $R_1$)
$d_3 = 0.9025$   $n_2 = 1.60000$ (*)
$r_4 = -0.6000$ (= $R_2$)

(Coefficients of power distribution of GRIN lens)
g = 0.61,   $h_4 = 2.2$,   $h_6 = -30$ -continued $$\left|\frac{2I}{\phi}\right| = 0.8, \quad \frac{1-n_0}{R_2 \cdot n_0 \cdot g \cdot \sin(gZ)} = 1.959$$

$$\left|\frac{R_2}{I}\right| = 1.5, \quad \left|\frac{R_2}{R_1}\right| = 0$$

Embodiment 9
f = 0.707,  F = 3.01,  2ω = 95.7°
I = 0.6,  φ = 0.9

$r_1 = \infty$
$d_1 = 0.4000$  $n_1 = 1.51633$  $\nu_1 = 64.15$
$r_2 = \infty$ (stop)
$d_2 = 0$
$r_3 = \infty$ (= $R_1$)
$d_3 = 0.7888$  $n_2 = 1.7000$ (*)
$r_4 = -0.7000$ (= $R_2$)
$d_4 = 0.4700$
$r_5 = \infty$
$d_5 = 0.3000$  $n_3 = 1.51633$  $\nu_3 = 64.15$
$r_6 = \infty$ (Coefficients of power distribution of GRIN lens)
g = 0.65,  $h_4$ = 2,  $h_6$ = 10

$$\left|\frac{2I}{\phi}\right| = 1.333, \quad \frac{1-n_0}{R_2 \cdot n_0 \cdot g \cdot \sin(gZ)} = 1.845$$

$$\left|\frac{R_2}{I}\right| = 1.167, \quad \left|\frac{R_2}{R_1}\right| = 0$$

Embodiment 10
f = 0.495,  F = 3.00,  2ω = 68.8°
I = 0.3,  φ = 0.6

$r_1 = \infty$ (stop)
$d_1 = 0$
$r_2 = 0.9000$ (= $R_1$)
$d_2 = 0.7761$  $n_1 = 1.6000$ (*)
$r_3 = -0.6000$ (= $R_2$)

(Coefficients of power distribution of GRIN lens)
g = 1.0,  $h_4$ = 0,  $h_6$ = 0

$$\left|\frac{2I}{\phi}\right| = 1.0, \quad \frac{1-n_0}{R_2 \cdot n_0 \cdot g \cdot \sin(gZ)} = 0.892$$

$$\left|\frac{R_2}{I}\right| = 2.0, \quad \left|\frac{R_2}{R_1}\right| = 0.667$$

Embodiment 11
f = 0.535,  F = 2.99,  2ω = 63.2°
I = 0.3,  φ = 0.6

$r_1 = \infty$ (stop)
$d_1 = 0$
$r_2 = 0.9000$ (= $R_1$)
$d_2 = 0.8794$  $n_1 = 1.6000$ (*)
$r_3 = -0.9000$ (= $R_2$)

(Coefficients of power distribution of GRIN lens)
g = 1.0  $h_4$ = 0,  $h_6$ = 0

$$\left|\frac{2I}{\phi}\right| = 1.0, \quad \frac{1-n_0}{R_2 \cdot n_0 \cdot g \cdot \sin(gZ)} = 0.541$$

$$\left|\frac{R_2}{I}\right| = 3.0, \quad \left|\frac{R_2}{R_1}\right| = 1.0$$

Embodiment 12
f = 0.475,  F = 2.99,  2ω = 70.1°
I = 0.3,  φ = 0.65

$r_1 = \infty$ (stop)
$d_1 = 0$
$r_2 = 1.0000$ (= $R_1$)
$d_2 = 0.7435$  $n_1 = 1.60000$ (*)

-continued $r_3 = -0.5000$ (= $R_2$)

(Coefficients of power distribution of GRIN lens)
g = 1.0,  $h_4$ = 3,  $h_6$ = 0

$$\left|\frac{2I}{\phi}\right| = 0.923, \quad \frac{1-n_0}{R_2 \cdot n_0 \cdot g \cdot \sin(gZ)} = 1.108$$

$$\left|\frac{R_2}{I}\right| = 1.667, \quad \left|\frac{R_2}{R_1}\right| = 0.5$$

Embodiment 13
f = 0.507,  F = 3.01,  2ω = 65.0°
I = 0.3,  φ = 0.65

$r_1 = \infty$ (stop)
$d_1 = 0$
$r_2 = 0.7000$ (= $R_1$)
$d_2 = 0.8874$  $n_1 = 1.60000$ (*)
$r_3 = -0.7000$ (= $R_2$)

(Coefficients of power distribution of GRIN lens)
g = 1.0,  $h_4$ = 3,  $h_6$ = 0

$$\left|\frac{2I}{\phi}\right| = 0.923, \quad \frac{1-n_0}{R_2 \cdot n_0 \cdot g \cdot \sin(gZ)} = 0.697$$

$$\left|\frac{R_2}{I}\right| = 2.333, \quad \left|\frac{R_2}{R_1}\right| = 1.0$$

Embodiment 14
f = 0.317,  F = 3.00,  2ω = 108.9°
I = 0.3,  φ = 0.65

$r_1 = \infty$ (stop)
$d_1 = 0$
$r_2 = 1.0000$ (= $R_1$)
$d_2 = 0.6798$  $n_1 = 1.80000$ (*)
$r_3 = -0.5000$ (= $R_2$)

(Coefficients of power distribution of GRIN lens)
g = 1.5,  $h_4$ = 2.5,  $h_6$ = −0.5

$$\left|\frac{2I}{\phi}\right| = 0.923, \quad \frac{1-n_0}{R_2 \cdot n_0 \cdot g \cdot \sin(gZ)} = 0.696$$

$$\left|\frac{R_2}{I}\right| = 1.667, \quad \left|\frac{R_2}{R_1}\right| = 0.5$$

Embodiment 15
f = 0.201,  F = 2.99,  2ω = 87.8°
I = 0.15,  φ = 0.35

$r_1 = \infty$
$d_1 = 0.1500$  $n_1 = 1.51633$,  $\nu_1 = 64.15$
$r_2 = \infty$
$d_2 = 0$
$r_3 = \infty$ (stop)
$d_3 = 0.0500$
$r_4 = 0.4000$ (= $R_1$)
$d_4 = 0.2429$  $n_2 = 1.6500$ (*)
$r_5 = -0.3000$ (= $R_2$)

(Coefficients of power distribution of GRIN lens)
g = 2.5,  $h_4$ = 1.5,  $h_6$ = 1

$$\left|\frac{2I}{\phi}\right| = 0.857, \quad \frac{1-n_0}{R_2 \cdot n_0 \cdot g \cdot \sin(gZ)} = 0.921$$

$$\left|\frac{R_2}{I}\right| = 2.0, \quad \left|\frac{R_2}{R_1}\right| = 0.75$$

Embodiment 16
f = 0.236,  F = 3.04,  2ω = 71.5°
I = 0.15,  φ = 0.35

$r_1 = \infty$

-continued $d_1 = 0.500 \quad n_1 = 1.51633 \quad \nu_1 = 64.15$
$r_2 = \infty$
$d_2 = 0$
$r_3 = \infty \text{ (stop)}$
$d_3 = 0.0500$
$r_4 = 0.4500 \ (= R_1)$
$d_4 = 0.3785 \quad n_2 = 1.65000 \ (*)$
$r_5 = -0.3000 \ (= R_2)$ (Coefficients of power distribution of GRIN lens)
$g = 2, \quad h_4 = 4, \quad h_6 = -1.5$ $\left|\dfrac{2I}{\phi}\right| = 0.857, \quad \dfrac{1 - n_0}{R_2 \cdot n_0 \cdot g \cdot \sin(gZ)} = 0.910$ $\left|\dfrac{R_2}{I}\right| = 2.0, \quad \left|\dfrac{R_2}{R_1}\right| = 0.667$ Embodiment 17

$f = 0.830, \quad F = 3.00, \quad 2\omega = 80.6°$
$I = 0.6, \quad \phi = 1.0$ $r_1 = \infty$
$d_1 = 0.4000 \quad n_1 = 1.51633 \quad \nu_1 = 64.15$
$r_2 = \infty$
$d_2 = 0$
$r_3 = \infty \text{ (stop)}$
$d_3 = 0.1000$
$r_4 = 2.5000 \ (= R_1)$
$d_4 = 0.5850 \quad n_2 = 1.60000 \ (*)$
$r_5 = -0.8000 \ (= R_2)$
$d_5 = 0.3900$
$r_6 = \infty$
$d_6 = 0.6000 \quad n_3 = 1.51633 \quad \nu_3 = 64.15$
$r_7 = \infty$ (Coefficients of power distribution of GRIN lens)
$g = 0.61, \quad h_4 = 2.2, \quad h_6 = -30$ $\left|\dfrac{2I}{\phi}\right| = 1.2, \quad \dfrac{1 - n_0}{R_2 \cdot n_0 \cdot g \cdot \sin(gZ)} = 2.2$ $\left|\dfrac{R_2}{I}\right| = 1.333, \quad \left|\dfrac{R_2}{R_1}\right| = 0.32$ Embodiment 18

$f = 0.625, \quad F = 3.00, \quad 2\omega = 76.3°$
$I = 0.4, \quad \phi = 0.9$ $r_1 = \infty$
$d_1 = 0.4000 \quad n_1 = 1.51633 \quad \nu_1 = 64.15$
$r_2 = \infty$
$d_2 = 0$
$r_3 = \infty \text{ (stop)}$
$d_3 = 0.1000$
$r_4 = 0.14000 \ (= R_1)$
$d_4 = 0.9581 \quad n_2 = 1.70000 \ (*)$
$r_5 = -0.7000 \ (= R_2)$ (Coefficients of power distribution of GRIN lens)
$g = 0.65, \quad h_4 = 2, \quad h_6 = 10$ $\left|\dfrac{2I}{\phi}\right| = 0.889, \quad \dfrac{1 - n_0}{R_2 \cdot n_0 \cdot g \cdot \sin(gZ)} = 1.552$ $\left|\dfrac{R_2}{I}\right| = 1.75, \quad \left|\dfrac{R_2}{R_1}\right| = 0.5$ In respective embodiments shown in the above, reference symbols $r_1, r_2, \ldots$ respectively represent radii of curvature of respective surfaces, in the order from the object side, including the stop and cover glass, reference symbols $d_1, d_2, \ldots$ respectively represent distances between respective surfaces in the order from the object side, reference symbols $n_1, n_2, \ldots$ respectively represent refractive indices of the lens, and reference symbol $\nu_1$ and $\nu_2$ represent Abbe's number of the lens made of a homogeneous medium. In those embodiments wherein the stop is provided on the lens surface or on the surface of the plane-parallel plate or the stop is provided at the cemented surface between the plane-parallel plate and GRIN lens, the stop and the surface, on which the stop is provided, are shown separately and the distance between the stop and said surface is shown as 0. For the GRIN lens, the refractive index of the central portion thereof is shown and is marked with an asterisk (*).

Figure 9:
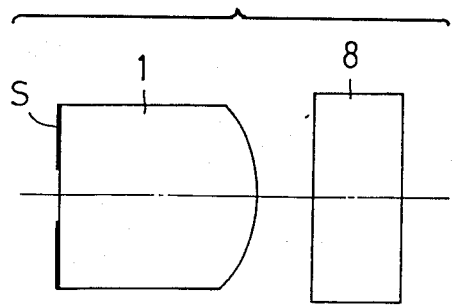
FIG. 9 shows a sectional view of Embodiment 1 of the present invention.

Out of respective embodiments shown in the above, Embodiment 1 has the lens configuration as shown in FIG. 9. That is, Embodiment 1 comprises a GRIN lens 1, which is formed as a plano-convex single lens and arranged that a stop S is provided on the front surface thereof, and a cover glass 8.

Figure 10:
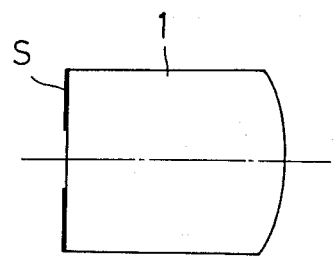
FIG. 10 shows a sectional view of Embodiments 2, 3, 4, 5 and 7 of the present invention.

Embodiments 2, 3, 4, 5 and 7 respectively have the lens configuration as shown in FIG. 10. That is, each of said embodiments comprises a GRIN lens only which is formed as a plano-convex single lens and arranged that a stop S is provided on the front surface thereof.

Figure 11:
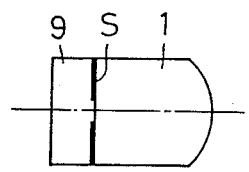
FIG. 11 shows a sectional view of Embodiments 6 and 8 of the present invention.

Embodiments 6 and 8 respectively have the lens configuration as shown in FIG. 11. That is, each of said embodiments comprises a plane-parallel plate 9 made of a homogeneous medium and a GRIN lens 1 having a plano-convex shape which are cemented together, and a stop S is provided at the cemented surface between them.

Figure 12:
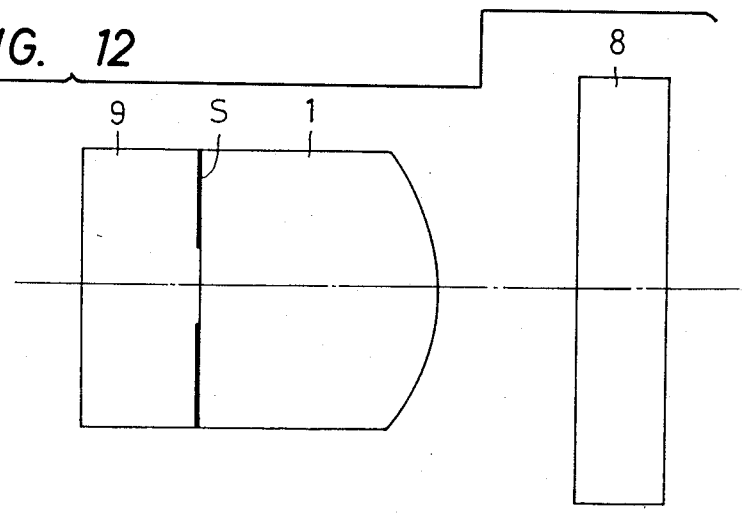
FIG. 12 shows a sectional view of Embodiment 9 of the present invention.

Embodiment 9 has the lens configuration as shown in FIG. 12. That is, Embodiment 9 comprises a plane-parallel plate 9 made of a homogeneous medium and a GRIN lens 1 having a plano-convex shape which are cemented together and arranged that a stop S is provided at the cemented surface between them. Embodiment 9 further comprises a cover glass 8 arranged on the image side of said GRIN lens 1.

Figure 13:
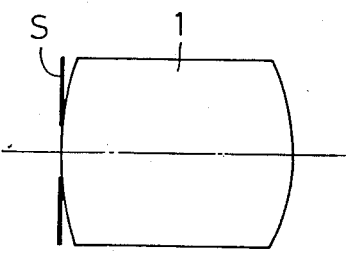
FIG. 13 shows a sectional view of Embodiments 10, 11, 12, 13 and 14 of the present invention.

Embodiments 10, 11, 12, 13 and 14 respectively have the lens configuration as shown in FIG. 13. That is, each of said embodiments comprises a GRIN lens 1 having a biconvex shape and a stop S arranged in front of said GRIN lens 1.

Figure 14:
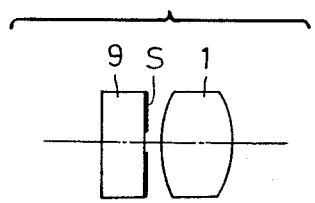
FIG. 14 shows a sectional view of Embodiments 15, 16 and 18 of the present invention.

Embodiments 15, 16 and 18 respectively have the lens configuration as shown in FIG. 14. That is, each of said embodiments comprises a plane-parallel plate 9, which is made of a homogeneous medium and arranged that a stop S is provided on the rear surface thereof, and a GRIN lens 1 having a biconvex shape.

Figure 15:
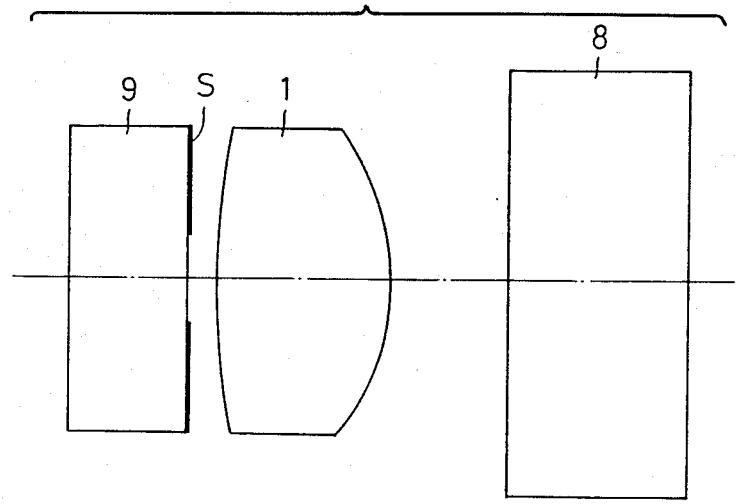
FIG. 15 shows a sectional view of Embodiment 17 of the present invention.
Figure 16:
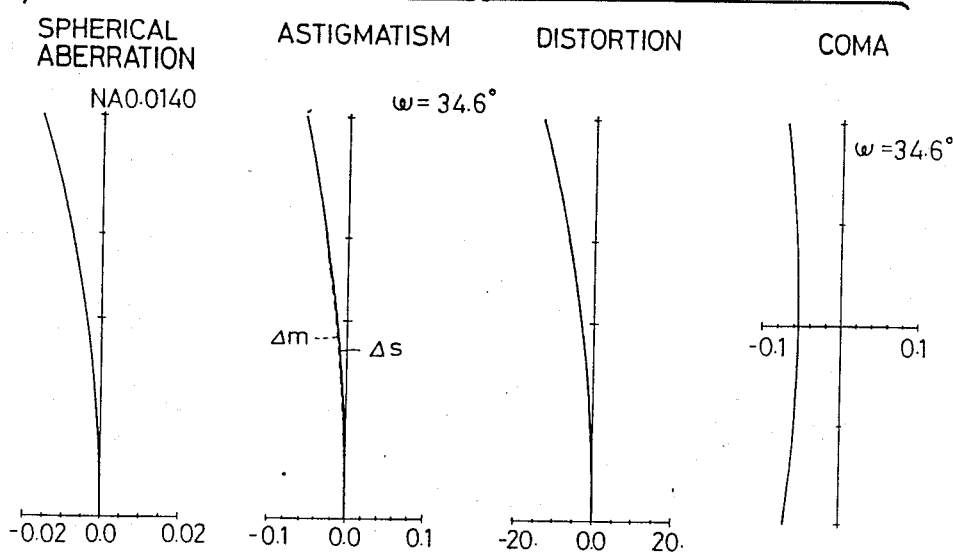
Figure 17:
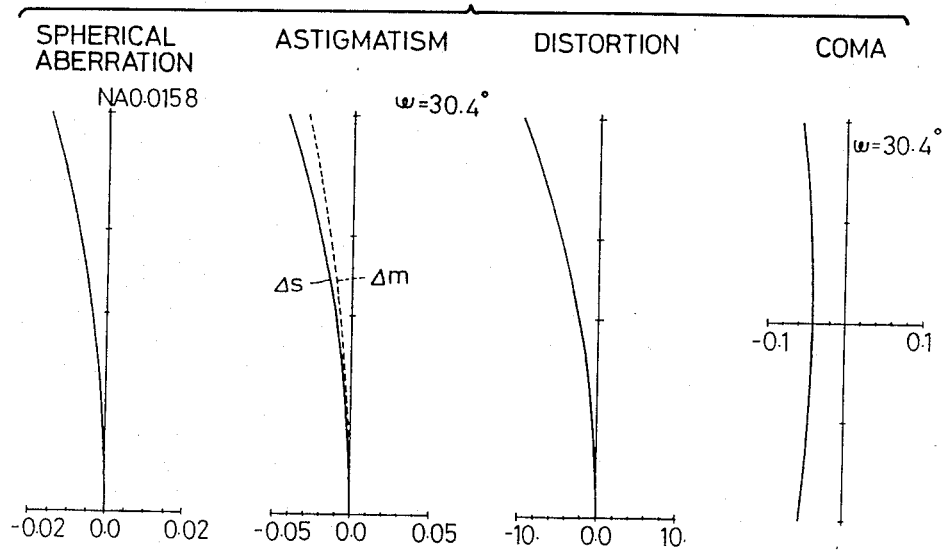
Figure 20:
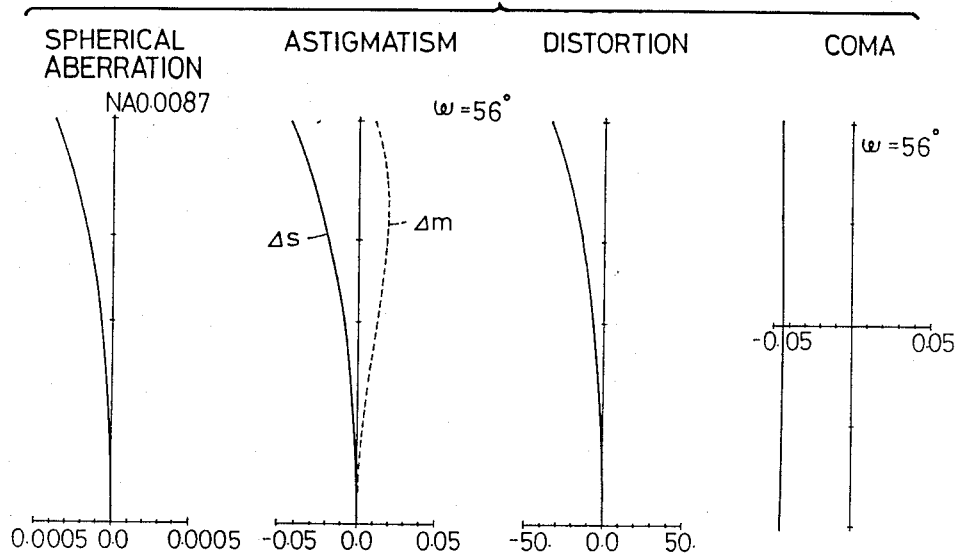
Figure 21:
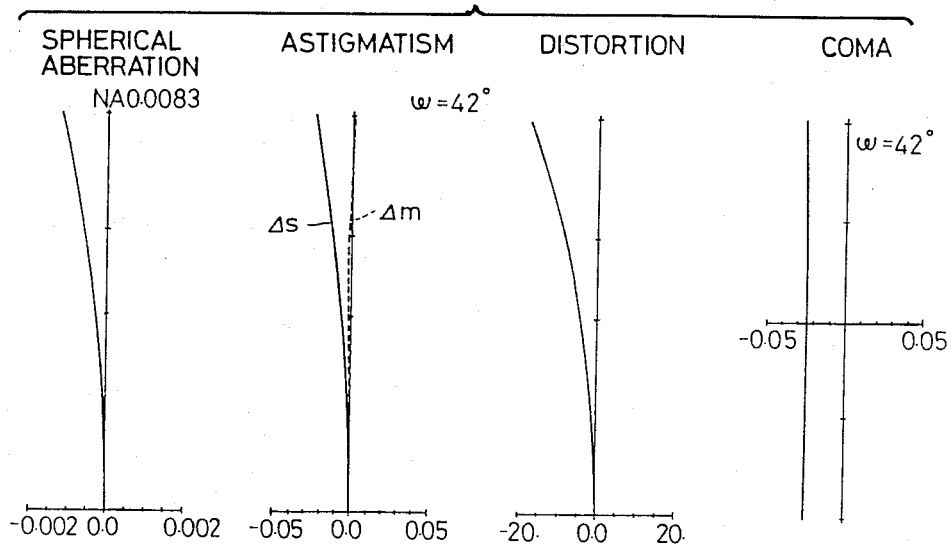
Figure 22:
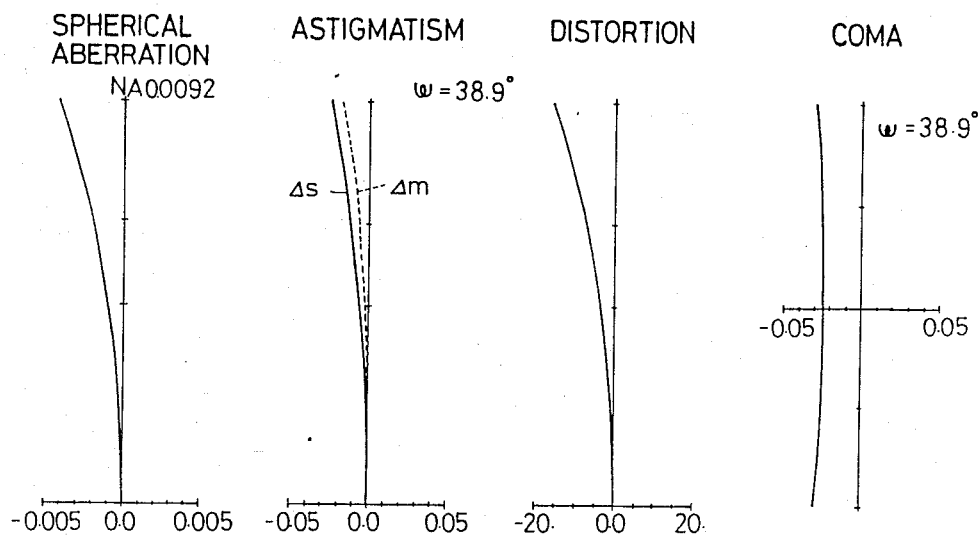
Figure 23:
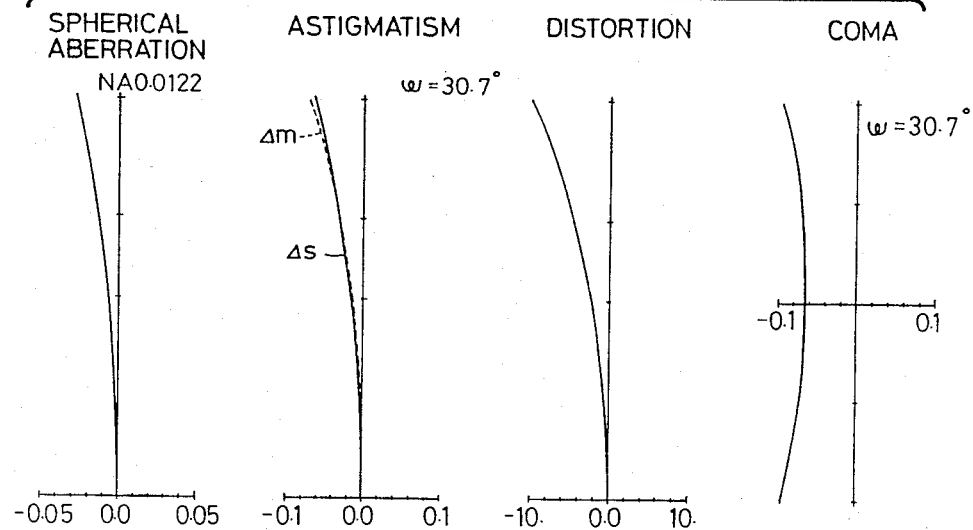
Figure 24:
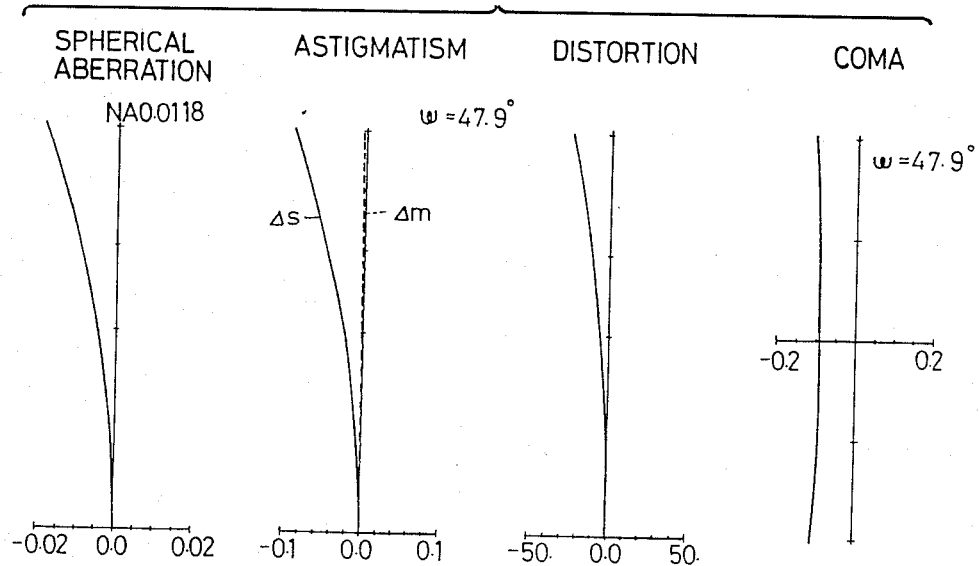
Figure 25:
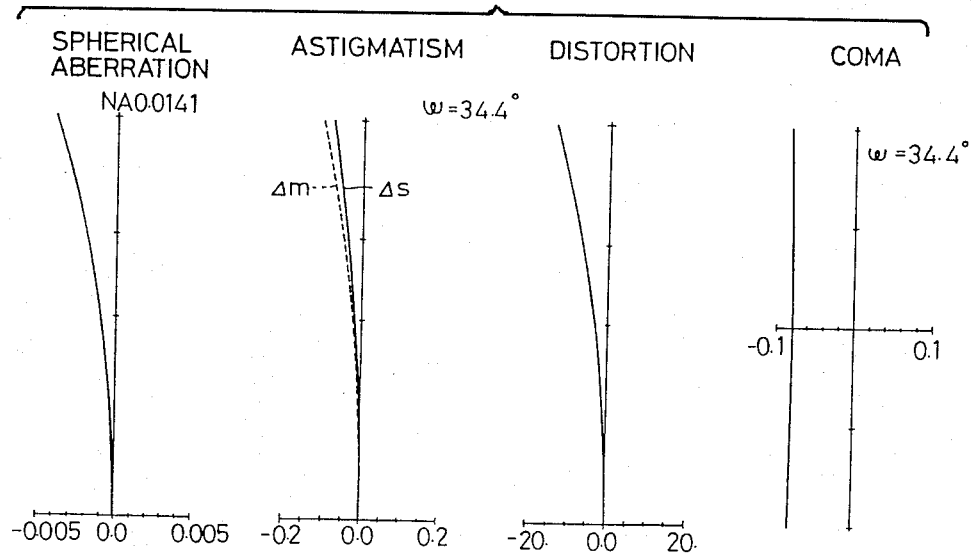
Figure 26:
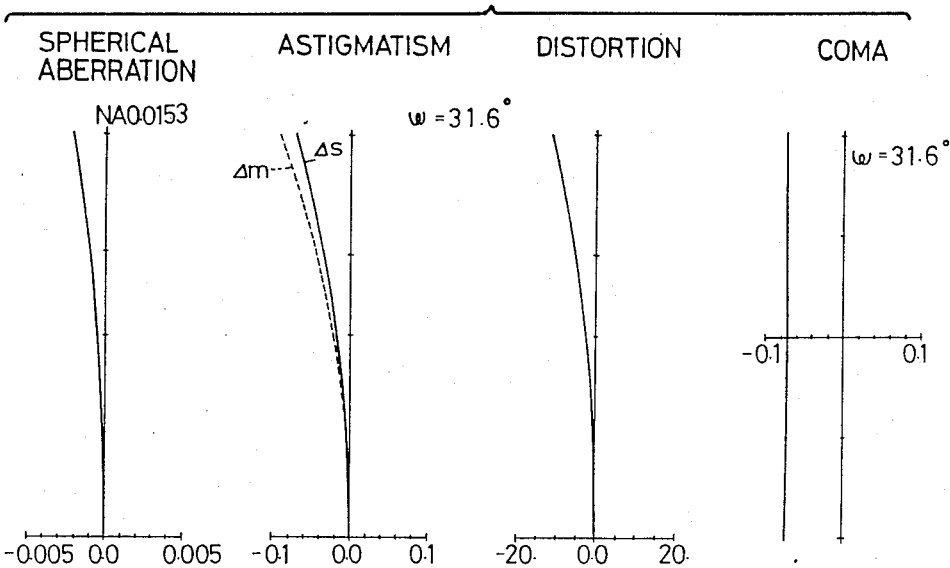
Figure 27:
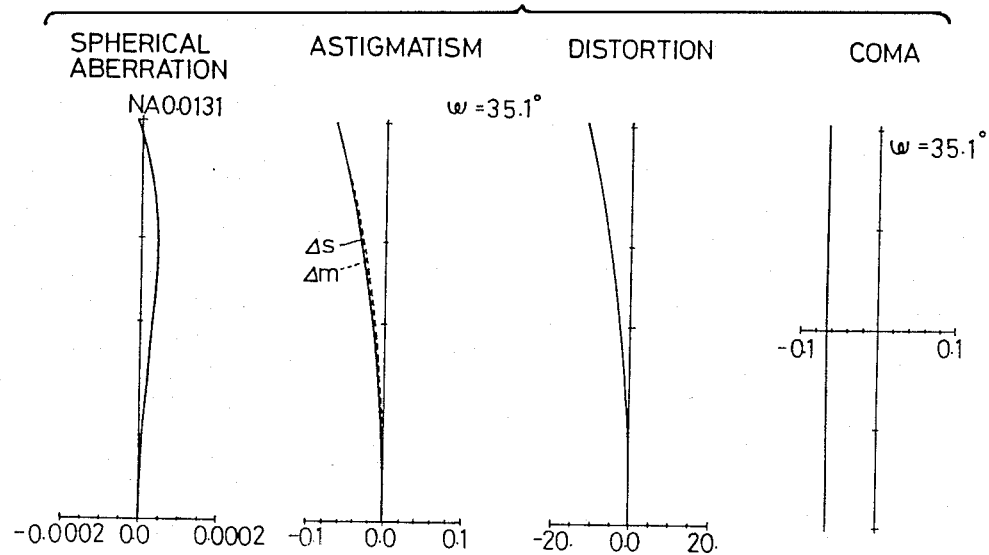
Figure 28:
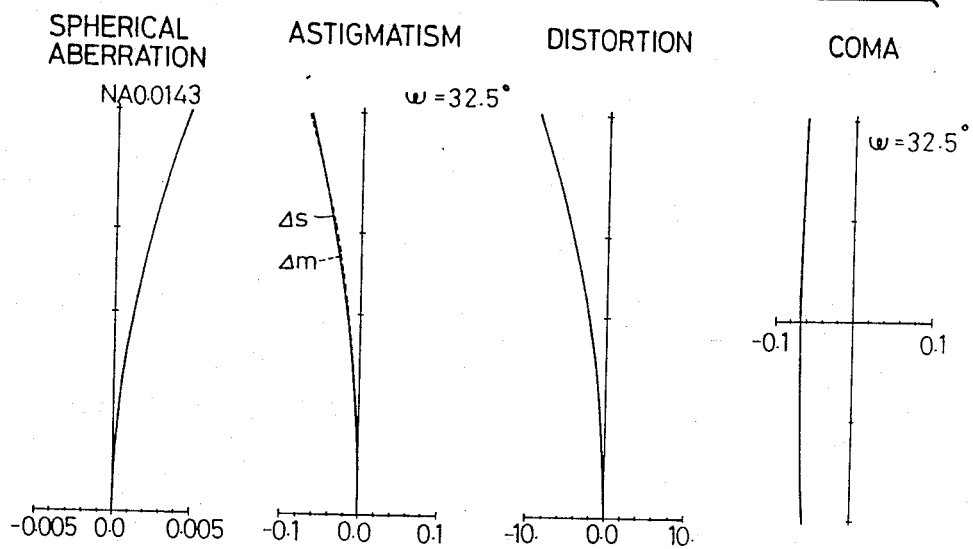
Figure 29:
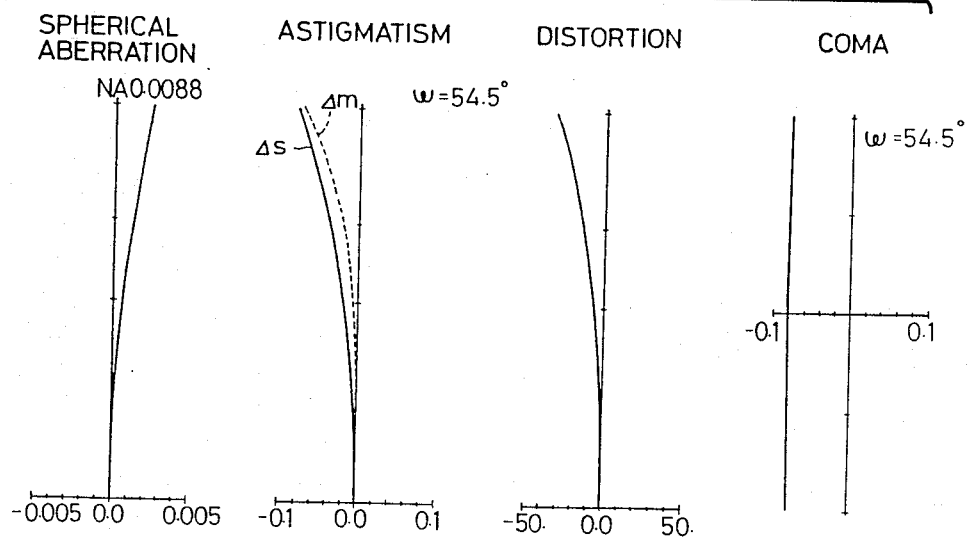
Figure 32:
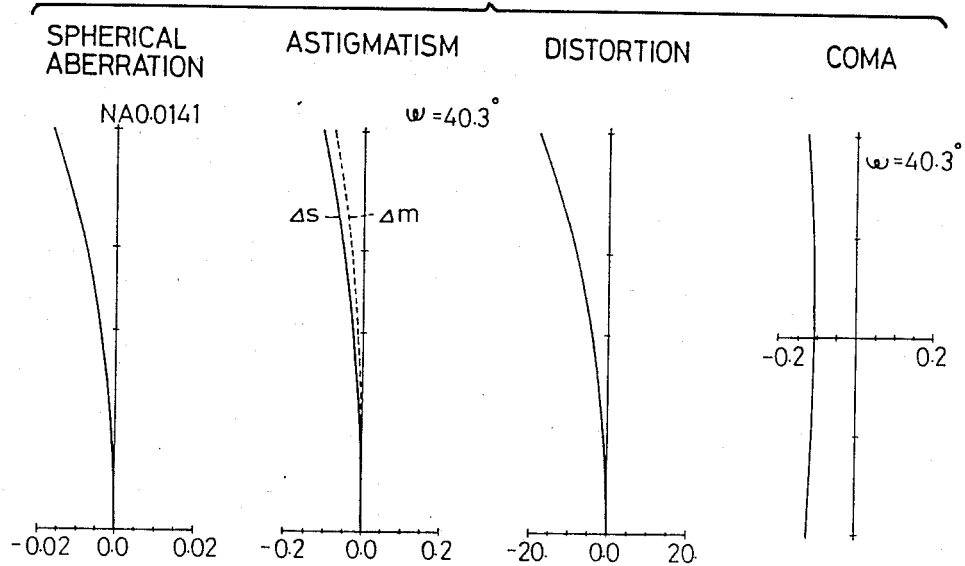
Figure 33:
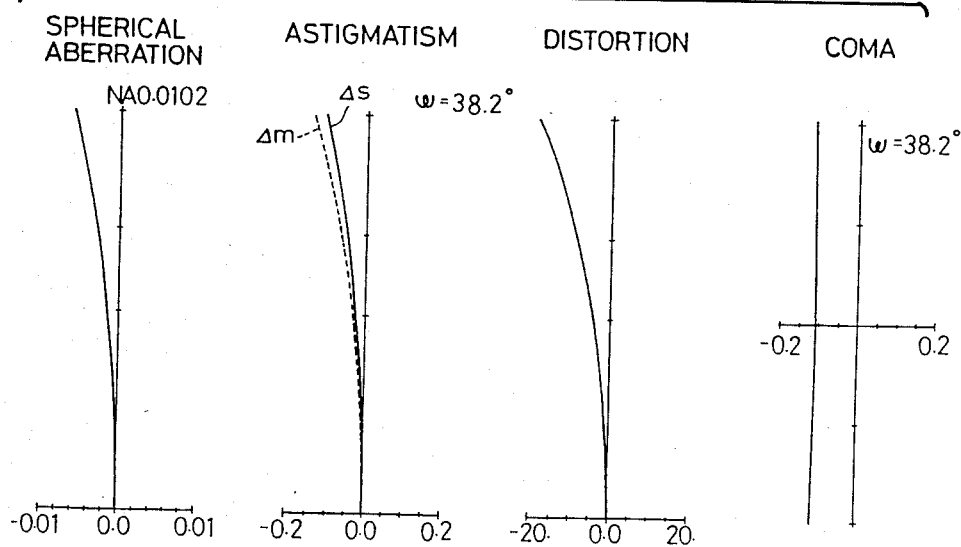

Embodiment 17 has the lens configuration as shown in FIG. 15. That is, Embodiment 17 comprises a plane-parallel plate made of a homogeneous medium and arranged that a stop S is provided on the rear surface thereof, a GRIN lens 1 having a biconvex shape, and a cover glass 8.

Aberration curves of Embodiments 1 through 18 described so far are as shown in FIGS. 16 through 33 respectively.

What is claimed is:

1. An objective for an endoscope comprising a GRIN lens whose surface on the object side is arranged as a planar surface or convex surface and whose surface on the image side is arranged as a convex surface, and an aperture stop located on the object side of said GRIN lens, said GRIN lens being arranged that the refractive index n thereof is expressed by the formula shown below when the refractive index of the central portion thereof is represented by reference symbol $n_0$ and the radial distance from the optical axis is represented by reference symbol r, said objective for an endoscope fulfilling the conditions (1), (2) and (3) shown below:

$$n^2(r) = n_0^2 \{1 - (gr)^2 + h_4(gr)^4 + h_6(gr)^6 + \ldots \}$$

$$1.4 \geq |2I/\phi| \geq 0.6 \quad (1)$$

$$0.5 \leq \frac{1 - n_0}{R_2 \cdot n_0 \cdot g \cdot \sin(gZ)} \leq 3 \quad (2)$$

$$|R_2/R_1| \leq 1.0 \quad (3)$$

where, reference symbol g represents a parameter showing the degree of the gradient of the refractive index, reference symbols $h_4$, $h_6$, ... respectively represent the coefficients of distribution of refractive indices in the terms of the fourth order, sixth order and so on, reference symbol I represents the image height, reference symbol $\phi$ represents the outer diameter of the GRIN lens, reference symbol Z represents the thickness of the central portion of the GRIN lens, and reference symbol $R_1$ and $R_2$ respectively represent radii of curvature of the surface on the object side and surface on the image side of the GRIN lens.

2. An objective for an endoscope according to claim 1 further fulfilling the conditions (4), (5) and (6) shown below:

$$|R_2/I| \leq 3 \quad (4)$$

$$g \geq 0.58 \quad (5)$$

$$h_4 \geq 0 \quad (6).$$

3. An objective for an endoscope according to claim 2 comprising said GRIN lens and a cover glass wherein said GRIN lens is arranged to have a plano-convex shape and arranged that said aperture stop is provided on the front surface of said GRIN lens, said objective for an endoscope having the following numerical data:

| f = 0.491, | F = 2.99, | $2\omega = 69.2°$ |
| I = 0.3, | $\phi = 0.6$ | |

| $r_1 = \infty$ (stop) | | |
| $d_1 = 0$ | | |
| $r_2 = \infty$ ( = $R_1$) | | |
| $d_2 = 0.6632$ | $n_1 = 1.6000$ (*) | |
| $r_3 = -0.4500$ ( = $R_2$) | | |
| $d_3 = 0.1900$ | | |
| $r_4 = \infty$ | | |
| $d_4 = 0.3000$ | $n_2 = 1.51633$ | $\nu = 64.15$ |
| $r_5 = \infty$ | | |

| (Coefficients of power distribution of GRIN lens) | | |
| g = 1.0, | $h_4 = 0$, | $h_6 = 0$ |

$$\left|\frac{2I}{\phi}\right| = 1.0, \quad \frac{1 - n_0}{R_2 \cdot n_0 \cdot g \cdot \sin(gZ)} = 1.354$$

$$\left|\frac{R_2}{I}\right| = 1.5, \quad \left|\frac{R_2}{R_1}\right| = 0$$

where, reference symbols $r_1$, $r_2$, ... respectively represent radii of curvature of respective surfaces, in the order from the object side, including the stop and cover glass, reference symbols $d_1$, $d_2$, ... respectively represent distances between respective surfaces in the order from the object side, reference symbols $n_1$, $n_2$, ... respectively represent refractive indices of the lens, and reference symbol $\nu_2$ represents Abbe's number of the lens made of a homogeneous medium, and where, for the GRIN lens, the refractive index of the central portion thereof is shown and is marked with an asterisk (*).

4. An objective for an endoscope according to claim 2 comprising said GRIN lens wherein said GRIN is arranged to have a plano-convex shape and arranged that said aperture stop is provided on the front surface of said GRIN lens, said objective for an endoscope having the following numerical data:

| f = 0.551, | F = 2.99, | $2\omega = 60.8°$ |
| I = 0.3, | $\phi = 0.6$ | |

| $r_1 = \infty$ (stop) | |
| $d_1 = 0$ | |
| $r_2 = \infty$ ( = $R_1$) | |
| $d_2 = 0.7363$ | $n_1 = 1.6000$ (*) |
| $r_3 = -0.6000$ ( = $R_2$) | |

| (Coefficients of power distribution of GRIN lens) | | |
| g = 1.0, | $h_4 = 0$, | $h_6 = 0$ |

$$\left|\frac{2I}{\phi}\right| = 1.0, \quad \frac{1 - n_0}{R_2 \cdot n_0 \cdot g \cdot \sin(gZ)} = 0.892$$

$$\left|\frac{R_2}{I}\right| = 2.0, \quad \left|\frac{R_2}{R_1}\right| = 0$$

where, reference symbols $r_1$, $r_2$ and $r_3$ respectively represent radii of curvature of respective surfaces, in the order from the object side, including the stop reference symbols $d_1$ and $d_2$ respectively represent distances between respective surfaces in the order form the object side, and reference symbol $n_1$ represents refractive index of the lens, and where, for the GRIN lens, the refractive index of the central portion thereof is shown and is marked with an asterisk (*).

5. An objective for an endoscope according to claim 2 comprising said GRIN lens wherein said GRIN lens is arranged to have a plano-convex shape and arranged that said aperture stop is provided on the front surface of said GRIN lens, said objective for an endoscope having the following numerical data:

| f = 0.589, | F = 2.99, | $2\omega = 56.6°$ |
| I = 0.3, | $\phi$ 0.6 | |

| $r_1 = \infty$ (stop) | |
| $d_1 = 0$ | |
| $r_2 = \infty$ ( = $R_1$) | |
| $d_2 = 0.7868$ | $n_1 = 1.6000$ (*) |
| $r_3 = -0.7500$ ( = $R_2$) | |

| (Coefficients of power distribution of GRIN lens) | | |
| g = 1.0, | $h_4 = 0$, | $h_6 = 0$ |

$$\left|\frac{2I}{\phi}\right| = 1.0, \quad \frac{1 - n_0}{R_2 \cdot n_0 \cdot g \cdot \sin(gZ)} = 0.706$$

$$\left|\frac{R_2}{I}\right| = 2.5, \quad \left|\frac{R_2}{R_1}\right| = 0$$

where, reference symbols $r_1$, $r_2$ and $r_3$ respectively represent radii of curvature of respective surfaces, in the order from the object side, including the stop, reference symbols $d_1$ and $d_2$ respectively represent distances beteen respective surfaces in the order from the object side, and reference symbol $n_1$ represents refractive index of the lens, and where, for the GRIN lens, the refractive index of the central portion thereof is shown and is marked with an asterisk (*).

6. An objective for an endoscope according to claim 2 comprising said GRIN lens wherein said GRIN lens is arranged to have a plano-convex shape and arranged that said aperture stop is provided on the front surface of said GRIN lens, said objective for an endoscope having the following numerical data:

| f = 0.490, | F = 3.01, | 2ω = 67.6° |
|---|---|---|
| I = 0.3, | φ = 0.65 | |
| $r_1 = \infty$ (stop) | | |
| $d_1 = 0$ | | |
| $r_2 = \infty \, (= R_1)$ | | |
| $d_2 = 0.6774$ | $n_1 = 1.6000$ (*) | |
| $r_3 = -0.4500 \, (= R_2)$ | | |
| (Coefficients of power distribution of GRIN lens) | | |
| g = 1.0, | $h_4 = 3$, | $h_6 = 0$ |
| $\left|\dfrac{2I}{\phi}\right| = 0.923,$ | $\dfrac{1-n_0}{R_2 \cdot n_0 \cdot g \cdot \sin(gZ)} = 1.330$ | |
| $\left|\dfrac{R_2}{I}\right| = 1.5$ | $\left|\dfrac{R_2}{R_1}\right| = 0$ | | where, reference symbols $r_1$, $r_2$ and $r_3$ respectively represent radii of curvature of respective surfaces, in the order from the object side, including the stop reference symbols $d_1$ and $d_2$ respectively represent distances between respective surfaces in the order from the object side, and reference symbols $n_1$ represents refractive index of the lens, and where, for the GRIN lens, the refractive index of the central portion thereof is shown and is marked with an asterisk (*).

7. An objective for an endoscope according to claim 2 comprising said GRIN lens wherein said GRIN lens is arranged to have a plano-convex shape and arranged that said aperture stop is provided on the front surface of said GRIN lens, said objective for an endoscope having the following numerical data:

| f = 0.310, | F = 2.99, | 2ω = 111.9° |
|---|---|---|
| I = 0.3, | φ = 0.65 | |
| $r_1 = \infty$ (stop) | | |
| $d_1 = 0$ | | |
| $r_2 = \infty \, (= R_1)$ | | |
| $d_2 = 0.6238$ | $n_1 = 1.8000$ (*) | |
| $r_3 = -0.4500 \, (= R_2)$ | | |
| (Coefficients of power distribution of GRIN lens) | | |
| g = 1.5, | $h_4 = 2.5$, | $h_6 = -0.5$ |
| $\left|\dfrac{2I}{\phi}\right| = 0.923,$ | $\dfrac{1-n_0}{R_2 \cdot n_0 \cdot g \cdot \sin(gZ)} = 0.818$ | |
| $\left|\dfrac{R_2}{I}\right| = 1.5$ | $\left|\dfrac{R_2}{R_1}\right| = 0$ | | where, reference symbols $r_1$, $r_2$ and $r_3$ respectively represent radii of curvature of respective surfaces, in the order from the object side, including the stop, reference symbols $d_1$ and $d_2$ respectively represent distances between respective surfaces in the order from the object side, and reference symbol $n_1$ represents refractive index of the lens, and where, for the GRIN lens, the refractive index of the central portion thereof is shown and is marked with an asterisk (*).

8. An objective for an endoscope according to claim 2 comprising a plane-parallel plate made of a homogeneous medium and said GRIN lens wherein said GRIN lens has a plano-convex shape, said plane-parallel plate and said GRIN lens are cemented together, and said aperture stop is provided at the cemented surface between said plane-parallel plate and said GRIN lens, said objective for an endoscope having the following numerical data:

| f = 0.203, | F = 2.98, | 2ω = 83.9° | |
|---|---|---|---|
| I = 0.15, | φ = 0.35 | | |
| $r_1 = \infty$ | | | |
| $d_1 = 0.1500$ | $n_1 = 1.51633$ | $\nu_1 = 64.15$ | |
| $r_2 = \infty$ (stop) | | | |
| $d_2 = 0$ | | | |
| $r_3 = \infty \, (= R_1)$ | | | |
| $d_3 = 0.3930$ | $n_2 = 1.65000$ (*) | | |
| $r_2 = -0.2400 \, (= R_2)$ | | | |
| (Coefficients of power distribution of GRIN lens) | | | |
| g = 2.5, | $h_4 = 1.5$, | $h_6 = 1$ | |
| $\left|\dfrac{2I}{\phi}\right| = 0.857,$ | $\dfrac{1-n_0}{R_2 \cdot n_0 \cdot g \cdot \sin(gZ)} = 0.789$ | | |
| $\left|\dfrac{R_2}{I}\right| = 1.6$ | $\left|\dfrac{R_2}{R_1}\right| = 0$ | | | where, reference symbols $r_1$, $r_2$, . . . respectively represent radii of curvature of respective surfaces, in the order from the object side, including the stop, reference symbols $d_1$, $d_2$, . . . respectively represent distances between respective surfaces in the order from the object side, reference symbols $n_1$ and $n_2$ respectively represent refractive indices of the lens, and reference symbol $\nu_1$ represents Abbe's number of the lens made of a homogeneous medium, and where, for the GRIN lens, the refractive index of the central portion thereof is shown and is marked with an asterisk (*).

9. An objective for an endoscope according to claim 2 comprising said GRIN lens wherein said GRIN lens is arranged to have a plano-convex shape and arranged that said aperture stop is provided on the front surface of said GRIN lens, said objective for an endoscope having the following numerical data:

| f = 0.219, | F = 2.99, | 2ω = 77.8° |
|---|---|---|
| I = 0.15, | φ = 0.35 | |
| $r_1 = \infty$ (stop) | | |
| $d_1 = 0$ | | |
| $r_2 = \infty \, (= R_1)$ | | |
| $d_1 = 0.3192$ | $n_1 = 1.65000$ (*) | |
| $r_3 = -0.2000 \, (= R_2)$ | | |
| (Coefficients of power distribution of GRIN lens) | | |
| g = 2, | $h_4 = 4$, | $h_6 = -1.5$ |
| $\left|\dfrac{2I}{\phi}\right| = 0.857$ | $\dfrac{1-n_0}{R_2 \cdot n_0 \cdot g \cdot \sin(gZ)} = 1.573$ | |
| $\left|\dfrac{R_2}{I}\right| = 1.333$ | $\left|\dfrac{R_2}{R_1}\right| = 0$ | | where, reference symbols $r_1$, $r_2$ and $r_3$ respectively represent radii of curvature of respective surfaces, in the order from the object side, including the stop, reference symbols $d_1$ and $d_2$ respectively represent distances between respective surfaces in the order from the object side, and reference symbol $n_1$ represents refractive index of the lens, and where, for the GRIN lens, the refractive index of the central portion thereof is shown and is marked with an asterisk (*).

10. An objective for an endoscope according to claim 2 comprising a plane-parallel plate made of a homogeneous medium and said GRIN lens wherein said GRIN lens has a plano-convex shape, said plane-parallel plate and said GRIN lens are cemented together, and said aperture stop is provided at the cemented surface between said plane-parallel plate and said GRIN lens, said objective for an endoscope having the following numerical data:

| $f = 0.734$, | $F = 3.00$, | $2\omega = 61.4°$ |
|---|---|---|
| $I = 0.4$, | $\phi = 1.0$ | |
| $r_1 = \infty$ | | |
| $d_1 = 0.4000$ | $n_1 = 1.51633$ | $\nu_1 = 64.15$ |
| $r_2 = \infty$ (stop) | | |
| $d_2 = 0$ | | |
| $r_3 = \infty$ (= $R_1$) | | |
| $d_3 = 0.9025$ | $n_2 = 1.60000$ (*) | |
| $r_4 = -0.6000$ (= $R_2$) | | |

(Coefficients of power distribution of GRIN lens)

$g = 0.61$, $h_4 = 2.2$, $h_6 = -30$ $$\left|\frac{2I}{\phi}\right| = 0.8, \quad \frac{1-n_0}{R_2 \cdot n_0 \cdot g \cdot \sin(gZ)} = 1.959$$

$$\left|\frac{R_2}{I}\right| = 1.5, \quad \left|\frac{R_2}{R_1}\right| = 0$$

where, reference symbols $r_1, r_2, \ldots$ respectively represent radii of curvature of respective surfaces, in the order from the object side, including the stop, reference symbols $d_1, d_2, \ldots$ respectively represent distances between respective surfaces in the order from the object side, reference symbols $n_1$ and $n_2$ respectively represent refractive indices of the lens, and reference symbol $\nu_1$ represents Abbe's number of the lens made of a homogeneous medium, and where, for the GRIN lens, the refractive index of the central portion thereof is shown and is marked with an asterisk (*).

11. An objective for an endoscope according to claim 2 comprising a plane-parallel plate made of a homogeneous medium, said GRIN lens and a cover glass wherein said GRIN lens has a plano-convex shape, said plane-parallel plate and said GRIN lens are cemented together, and said aperture stop is provided at the cemented surface between said plane-parallel plate and said GRIN lens, said objective for an endoscope having the following numerical data:

| $f = 0.707$, | $F = 3.01$, | $2\omega = 95.7°$ |
|---|---|---|
| $I = 0.6$, | $\phi = 0.9$ | |
| $r_1 = \infty$ | | |
| $d_1 = 0.4000$ | $n_1 = 1.51633$ | $\nu_1 = 64.15$ |
| $r_2 = \infty$ (stop) | | |
| $d_2 = 0$ | | |
| $r_3 = \infty$ (= $R_1$) | | |
| $d_3 = 0.7888$ | $n_2 = 1.7000$ (*) | |
| $r_4 = -0.7000$ (= $R_2$) | | |
| $d_4 = 0.4700$ | | |
| $r_5 = \infty$ | | |
| $d_5 = 0.3000$ | $n_3 = 1.51633$ | $\nu_3 = 64.15$ |
| $r_6 = \infty$ | | |

(Coefficients of power distribution of GRIN lens)

$g = 0.65$, $h_4 = 2$, $h_6 = 10$, $$\left|\frac{2I}{\phi}\right| = 1.333, \quad \frac{1-n_0}{R_2 \cdot n_0 \cdot g \cdot \sin(gZ)} = 1.845$$

$$\left|\frac{R_2}{I}\right| = 1.167, \quad \left|\frac{R_2}{R_1}\right| = 0$$

where, reference symbols $r_1, r_2, \ldots$ respectively represent radii of curvature of respective surfaces, in the order from the object side, including the stop and cover glass, reference symbols $d_1, d_2, \ldots$ respectively represent distances between respective surfaces in the order from the object side, reference symbol $n_1, n_2, \ldots$ respectively represent refractive indices of the lens, and reference symbols $\nu_1$ and $\nu_3$ respectively represent Abbe's numbers of lenses made of a homogeneous medium, and where, for the GRIN lens, the refractive index of the central portion thereof is shown and is marked with an asterisk (*).

12. An objective for an endoscope according to claim 2 comprising said GRIN lens, which is arranged to have a biconvex shape, and said aperture stop arranged in front of said GRIN lens, said objective for an endoscope having the following numerical data:

| $f = 0.495$, | $F = 3.00$, | $2\omega = 68.8°$ |
|---|---|---|
| $I = 0.3$, | $\phi = 0.6$ | |
| $r_1 = \infty$ (stop) | | |
| $d_1 = 0$ | | |
| $r_2 = 0.9000$ (= $R_1$) | | |
| $d_2 = 0.7761$ | $n_1 = 1.6000$ (*) | |
| $r_3 = -0.6000$ (= $R_2$) | | |

(Coefficients of power distribution of GRIN lens)

$g = 1.0$, $h_4 = 0$, $h_6 = 0$ $$\left|\frac{2I}{\phi}\right| = 1.0, \quad \frac{1-n_0}{R_2 \cdot n_0 \cdot g \cdot \sin(gZ)} = 0.892$$

$$\left|\frac{R_2}{I}\right| = 2.0, \quad \left|\frac{R_2}{R_1}\right| = 0.667$$

where, reference symbols $r_1$, $r_2$ and $r_3$ respectively represent radii of curvature of respective surfaces, in the order from the object side, including the stop reference symbols $d_1$ and $d_2$ respectively represent distances between respective surfaces in the order from the object side, and reference symbol $n_1$ represents refractive index of the lens, and where, for the GRIN lens, the refractive index of the central portion thereof is shown and is marked with an asterisk (*).

13. An objective for an endoscope according to claim 2 comprising said GRIN lens, which is arranged to have a biconvex shape, and said aperture stop arranged in front of said GRIN lens, said objective for an endoscope having the following numerical data:

| $f = 0.535$, | $F = 2.99$, | $2\omega = 63.2°$ |
|---|---|---|
| $I = 0.3$, | $\phi = 0.6$ | |
| $r_1 = \infty$ (stop) | | |
| $d_1 = 0$ | | |
| $r_2 = 0.9000$ (= $R_1$) | | |
| $d_2 = 0.8794$ | $n_2 = 1.6000$ (*) | |

-continued $r_3 = -0.9000 (= R_2)$ (Coefficients of power distribution of GRIN lens)
$g = 1.0,$ $h_4 = 0,$ $h_6 = 0$ $\left|\frac{2I}{\phi}\right| = 1.0,$ $\frac{1 - n_0}{R_2 \cdot n_0 \cdot g \cdot \sin(gZ)} = 0.541$ $\left|\frac{R_2}{I}\right| = 3.0,$ $\left|\frac{R_2}{R_1}\right| = 1.0$ where, reference symbols $r_1$, $r_2$ and $r_3$ respectively represent radii of curvature of respective surfaces, in the order from the object side, including the stop, reference symbols $d_1$ and $d_2$ respectively represent distances between respective surfaces in the order from the object side, and reference symbol $n_1$ represents refractive index of the lens, and where, for the GRIN lens, the refractive index of the central portion thereof is shown and is marked with an asterisk (*).

14. An objective for an endoscope according to claim 2 comprising said GRIN lens, which is arranged to have a biconvex shape, and said aperture stop arranged in front of said GRIN lens, said objective for an endoscope having the following numerical data:

| $f = 0.475,$ | $F = 2.99,$ | $2\omega = 70.1°$ |
|---|---|---|
| $I = 0.3,$ | $\phi = 0.65$ | |
| $r_1 = \infty$ (stop) | | |
| $d_1 = 0$ | | |
| $r_2 = 1.0000 (= R_1)$ | | |
| $d_2 = 0.7435$ | $n_1 = 1.60000$ (*) | |
| $r_3 = -0.5000 (= R_2)$ | | |

(Coefficients of power distribution of GRIN lens)
$g = 1.0,$ $h_4 = 3,$ $h_6 = 0$ $\left|\frac{2I}{\phi}\right| = 0.923,$ $\frac{1 - n_0}{R_2 \cdot n_0 \cdot g \cdot \sin(gZ)} = 1.108$ $\left|\frac{R_2}{I}\right| = 1.667,$ $\left|\frac{R_2}{R_1}\right| = 0.5$ where, reference symbols $r_1$, $r_2$ and $r_3$ respectively represent radii of curvature of respective surfaces, in the order from the object side, including the stop, reference symbols $d_1$ and $d_2$ respectively represent distances between respective surfaces in the order from the object side, and reference symbol $n_1$ represents refractive index of the lens, and where, for the GRIN lens, the refractive index of the central portion thereof is shown and is marked with an asterisk (*).

15. An objective for an endoscope according to claim 2 comprising said GRIN lens, which is arranged to have a biconvex shape, and said aperture stop arranged in front of said GRIN lens, said objective for an endoscope having the following numerical data:

| $f = 0.507,$ | $F = 3.01,$ | $2\omega = 65.0°$ |
|---|---|---|
| $I = 0.3,$ | $\phi = 0.65$ | |
| $r_1 = \infty$ (stop) | | |
| $d_1 = 0$ | | |
| $r_2 = 0.7000 (= R_1)$ | | |
| $d_2 = 0.8774$ | $n_1 = 1.60000$ (*) | |
| $r_3 = -0.7000 (= R_2)$ | | |

(Coefficients of power distribution of GRIN lens)
$g = 1.0,$ $h_4 = 3,$ $h_6 = 0$ $\left|\frac{2I}{\phi}\right| = 0.923,$ $\frac{1 - n_0}{R_2 \cdot n_0 \cdot g \cdot \sin(gZ)} = 0.697$ $\left|\frac{R_2}{I}\right| = 2.333,$ $\left|\frac{R_2}{R_1}\right| = 1.0$ where, reference symbols $r_1$, $r_2$ and $r_3$ respectively represent radii of curvature of respective surfaces, in the order from the object side, including the stop, reference symbols $d_1$ and $d_2$ respectively represent distances between respective surfaces in the order from the object side, and reference symbol $n_1$ represents refractive index of the lens, and where, for the GRIN lens, the refractive index of the central portion thereof is shown and is marked with an asterisk (*).

16. An objective for an endoscope according to claim 2 comprising said GRIN lens, which is arranged to have a biconvex shape, and said aperture stop arranged in front of said GRIN lens, said objective for an endoscope having the following numerical data:

| $f = 0.317,$ | $F = 3.00,$ | $2\omega = 108.9°$ |
|---|---|---|
| $I = 0.3,$ | $\phi = 0.65$ | |
| $r_1 = \infty$ (stop) | | |
| $d_1 = 0$ | | |
| $r_2 = 1.0000 (= R_1)$ | | |
| $d_2 = 0.6798$ | $n_1 = 1.80000$ (*) | |
| $r_3 = -0.5000 (= R_2)$ | | |

(Coefficients of power distribution of GRIN lens)
$g = 1.5,$ $h_4 = 2.5,$ $h_6 = -0.5$ $\left|\frac{2I}{\phi}\right| = 0.923,$ $\frac{1 - n_0}{R_2 \cdot n_0 \cdot g \cdot \sin(gZ)} = 0.696$ $\left|\frac{R_2}{I}\right| = 1.667,$ $\left|\frac{R_2}{R_1}\right| = 0.5$ where, reference symbols $r_1$, $r_2$ and $r_3$ respectively represent radii of curvature of respective surfaces, in the order from the object side, including the stop, reference symbols $d_1$ and $d_2$ respectively represent distances between respective surfaces in the order from the object side, and reference symbol $n_1$ represents refractive index of the lens, and where, for the GRIN lens, the refractive index of the central portion thereof is shown and is marked with an asterisk (*).

17. An objective for an endoscope according to claim 2 comprising a plane-parallel plate, which is made of a homogeneous medium and arranged that said aperture stop is provided on the rear surface thereof, and said GRIN lens which is arranged to have a biconvex shape, said objective for an endoscope having the following numerical data:

| $f = 0.201,$ | $F = 2.99,$ | $2\omega = 87.8°$ | |
|---|---|---|---|
| $I = 0.15,$ | $\phi = 0.35$ | | |
| $r_1 = \infty$ | | | |
| $d_1 = 0.1500$ | $n_1 = 1.51633$ | $\nu_1 = 64.15$ | |
| $r_2 = \infty$ | | | |
| $d_2 = 0$ | | | |

-continued

```
r₃ = ∞ (stop)
d₃ = 0.0500
r₄ = 0.4000 (= R₁)
d₄ = 0.2429          n₂ = 1.65000 (*)
r₅ = −0.3000 (= R₂)
```

(Coefficients of power distribution of GRIN lens)
$g = 2.5$, $\quad h_4 = 1.5$, $\quad\quad h_6 = 1$ $$\left|\frac{2I}{\phi}\right| = 0.857, \quad \frac{1 - n_0}{R_2 \cdot n_0 \cdot g \cdot \sin(gZ)} = 0.921$$

$$\left|\frac{R_2}{I}\right| = 2.0, \quad \left|\frac{R_2}{R_1}\right| = 0.75$$

where, reference symbols $r_1$, $r_2$, ... respectively represent radii of curvature of respective surfaces, in the order from the object side, including the stop, reference symbols $d_1$ and $d_2$, ... respectively represent distances between respective surfaces in the order from the object side, reference symbols $n_1$ and $n_2$ respectively represent refractive indices of the lens, and reference symbol $\nu_1$ represents Abbe's number of the lens made of a homogeneous medium, and where, for the GRIN lens, the refractive index of the central portion thereof is shown and is marked with an asterisk (*).

18. An objective for an endoscope according to claim 2 comprising a plane-parallel plate, which is made of a homogeneous medium and arranged that said aperture stop is provided on the rear surface thereof, and said GRIN lens which is arranged to have a biconvex shape, said objective for an endoscope having the following numerical data:

| $f = 0.236$, | $F = 3.04$, | $2\omega = 71.5°$ |
|---|---|---|
| $I = 0.15$, | $\phi = 0.35$ | |

```
r₁ = ∞
d₁ = 0.1500          n₁ = 1.51633     ν₁ = 64.15
r₂ = ∞
d₂ = 0
r₃ = ∞ (stop)
d₃ = 0.0500
r₄ = 0.4500 (= R₁)
d₄ = 0.3785          n₂ = 1.65000 (*)
r₅ = −0.3000 (= R₂)
```

(Coefficients of power distribution of GRIN lens)
$g = 2$, $\quad h_4 = 4$, $\quad\quad h_6 = -1.5$ $$\left|\frac{2I}{\phi}\right| = 0.857, \quad \frac{1 - n_0}{R_2 \cdot n_0 \cdot g \cdot \sin(gZ)} = 0.910$$

$$\left|\frac{R_2}{I}\right| = 2.0, \quad \left|\frac{R_2}{R_1}\right| = 0.667$$

where, reference symbols $r_1$, $r_2$, ... respectively represent radii of curvature of respective surfaces, in the order from the object side, including the stop, reference symbols $d_1$, $d_2$, ... respectively represent distances between respective surfaces in the order from the object side, reference symbols $n_1$ and $n_2$ respectively represent refractive indices of the lens, and reference symbol $\nu_1$ represents Abbe's number of the lens made of a homogeneous medium, and where, for the GRIN lens, the refractive index of the central portion thereof is shown and is marked with an asterisk (*).

19. An objective for an endoscope according to claim 2 comprising a plane-parallel plate, which is made of a homoheneous medium and arranged that said aperture stop is provided on the rear surface thereof, said GRIN lens which is arranged to have a biconvex shape, and a cover glass, said objective for an endoscope having the following numerical data:

| $f = 0.830$, | $F = 3.00$, | $2\omega = 80.6°$ |
|---|---|---|
| $I = 0.6$, | $\phi = 1.0$ | |

```
r₁ = ∞
d₁ = 0.4000          n₁ = 1.51633     ν₁ = 64.15
r₂ = ∞
d₂ = 0
r₃ = ∞ (stop)
d₃ = 0.1000
r₄ = 2.5000 (= R₁)
d₄ = 0.3785          n₂ = 1.60000 (*)
r₅ = −0.8000 (= R₂)
d₅ = 0.3900
r₆ = ∞
d₆ = 0.6000          n₃ = 1.51633     ν₃ = 64.15
r₇ = ∞
```

(Coefficients of power distribution of GRIN lens)
$g = 0.61$, $\quad h_4 = 2.2$ $\quad\quad h_6 = -30$ $$\left|\frac{2I}{\phi}\right| = 1.2 \quad \frac{1 - n_0}{R_2 \cdot n_0 \cdot g \cdot \sin(gZ)} = 2.2$$

$$\left|\frac{R_2}{I}\right| = 1.333 \quad \left|\frac{R_2}{R_1}\right| = 0.32$$

where, reference symbols $r_1$, $r_2$, ... respectively represent radii of curvature of respective surfaces, in the order from the object side, including the stop and cover glass, reference symbols $d_1$, $d_2$, ... respectively represent distances between respective surfaces in the order from the object side, reference symbols $n_1$, $n_1$, ... respectively represent refractive indices of the lens, and reference symbols $\nu_1$ and $\nu_3$ respectively represent Abbe's number of the lens made of a homogeneous medium, and where, for the GRIN lens, the refractive index of the central portion thereof is shown and is marked with an asterisk (*).

20. An objective for an endoscope according to claim 2 comprising a plane-parallel plate, which is made of a homogeneous medium and arranged that said aperture stop is provided on the rear surface thereof, and said GRIN lens which is arranged to have a biconvex shape, said objective for an endoscope having the following numerical data:

| $f = 0.625$, | $F = 3.00$, | $2\omega = 76.3°$ |
|---|---|---|
| $I = 0.4$, | $\phi = 0.9$ | |

```
r₁ = ∞
d₁ = 0.4000          n₁ = 1.51633     ν₁ = 64.15
r₂ = ∞
d₂ = 0
r₃ = ∞ (stop)
d₃ = 0.1000
r₄ = 1.4000 (= R₁)
d₄ = 0.9581          n₂ = 1.70000 (*)
r₅ = −0.7000 (= R₂)
```

(Coefficients of power distribution of GRIN lens)
$g = 0.65$, $\quad h_4 = 2$, $\quad\quad h_6 = 10$ $$\left|\frac{2I}{\phi}\right| = 0.889, \quad \frac{1 - n_0}{R_2 \cdot n_0 \cdot g \cdot \sin(gZ)} = 1.552$$

-continued $$\left|\frac{R_2}{I}\right| = 1.75, \quad \left|\frac{R_2}{R_1}\right| = 0.5$$

where, reference symbols $r_1, r_2, \ldots$ respectively represent radii of curvature of respective surfaces, in the order from the object side, including the stop, reference symbols $d_1$ and $d_2, \ldots$ respectively represent distances between respective surfaces in the order from the object side, reference symbols $n_1$ and $n_2$ respectively represent refractive indices of the lens, and reference symbol $\nu_1$ represents Abbe's number of the lens made of a homogeneous medium, and where, for the GRIN lens, the refractive index of the central portion thereof is shown and is marked with an asterisk (*).

* * * * *